(12) United States Patent
Zeng (10) Patent No.: US 11,551,356 B2
(45) Date of Patent: Jan. 10, 2023

(54) OBJECT DETECTION METHOD, OBJECT DETECTION SYSTEM FOR 3D MAMMOGRAM, AND NON-TRANSITORY COMPUTER-READABLE STORAGE MEDIUM

(71) Applicant: INSTITUTE FOR INFORMATION INDUSTRY, Taipei (TW)

(72) Inventor: Yi-Chong Zeng, Taipei (TW)

(73) Assignee: INSTITUTE FOR INFORMATION INDUSTRY, Taipei (TW)

( * ) Notice: Subject to any disclaimer, the term of this patent is extended or adjusted under 35 U.S.C. 154(b) by 307 days.

(21) Appl. No.: 17/012,081

(22) Filed: Sep. 4, 2020

(65) Prior Publication Data
US 2022/0028062 A1   Jan. 27, 2022

(30) Foreign Application Priority Data
Jul. 27, 2020   (TW) .................................. 10912533.8

(51) Int. Cl.
G06T 7/00   (2017.01)
G06T 5/20   (2006.01)
(Continued)

(52) U.S. Cl.
CPC ............ *G06T 7/0012* (2013.01); *A61B 6/502* (2013.01); *A61B 6/5217* (2013.01); *G06T 5/20* (2013.01);
(Continued)

(58) Field of Classification Search
None
See application file for complete search history.

(56) References Cited

U.S. PATENT DOCUMENTS

| 5,598,481 | A | * | 1/1997 | Nishikawa | G06T 7/0012 |
| | | | | | 382/130 |
| 6,480,565 | B1 | * | 11/2002 | Ning | A61B 6/032 |
| | | | | | 378/20 |

(Continued)

FOREIGN PATENT DOCUMENTS

| CN | 100362964 C | 1/2008 | | |
| DE | 102006021036 A1 | * | 10/2007 | ........... G06T 7/0012 |
| KR | 20130011854 A | * | 1/2013 | ............. G06T 5/009 |

OTHER PUBLICATIONS

Y.-C. Zeng and C.-H. Tsai, "Detection of salient object using pixel blurriness," Proceedings of The 2012 Asia Pacific Signal and Information Processing Association Annual Summit and Conference, 2012, pp. 1-4. (Year: 2012).*

(Continued)

*Primary Examiner* — Vu Le
*Assistant Examiner* — Courtney Joan Nelson
(74) *Attorney, Agent, or Firm* — CKC & Partners Co., LLC (57) ABSTRACT

An object detection method for a 3D mammogram is disclosed. The object detection method comprises steps of: controlling N filters to execute a filtering computation in the 3D mammogram respectively to generate N 3D filtering images; computing a difference variation among the plurality of voxels to obtain a blurriness value of the plurality of voxels; using the blurriness value of the plurality of voxels in a decision module to execute a plurality of first decision operators to generate a plurality of first decision results, and using one of the plurality of first decision results to execute the plurality of second decision operators to generate a plurality of second decision results; and executing a final decision operator by using the plurality of first decision
(Continued)

results and the plurality of second decision results to generate a detection object of the 3D mammogram.

22 Claims, 6 Drawing Sheets

(51) Int. Cl.
    *G06T 7/70*     (2017.01)
    *A61B 6/00*     (2006.01)
    *G06T 11/00*     (2006.01)
    *G06V 20/64*     (2022.01)
    *A61B 6/02*     (2006.01)

(52) U.S. Cl.
    CPC .............. *G06T 7/70* (2017.01); *G06T 11/008* (2013.01); *G06V 20/64* (2022.01); *A61B 6/025* (2013.01); *G06T 2207/10112* (2013.01); *G06T 2207/30068* (2013.01)

(56) References Cited

U.S. PATENT DOCUMENTS

| | | | | |
|---|---|---|---|---|
| 8,848,866 | B2 * | 9/2014 | Virta | A61B 6/022 378/37 |
| 2007/0286470 | A1 * | 12/2007 | Bernard | G06T 7/0012 382/154 |
| 2011/0305313 | A1 * | 12/2011 | Sklansky | A61B 6/502 378/37 |

OTHER PUBLICATIONS

A machine translation of KR20130011854A (Year: 2013).*
A machine translation of DE-102006021036-A1 (Year: 2007).*
The office action of the corresponding Taiwanese application dated Jan. 4, 2021.

* cited by examiner

OBJECT DETECTION METHOD, OBJECT DETECTION SYSTEM FOR 3D MAMMOGRAM, AND NON-TRANSITORY COMPUTER-READABLE STORAGE MEDIUM

CROSS-REFERENCE TO RELATED APPLICATION

This application claims priority to and the benefit of Taiwan Application Serial Number 109125338, filed on Jul. 27, 2020, the entire content of which is incorporated herein by reference as if fully set forth below in its entirety and for all applicable purposes.

BACKGROUND

Field of Disclosure

The disclosure generally relates to an object detection method, system, and storage medium, and more particularly, to an object detection method, system, and storage medium for a 3D mammogram.

Description of Related Art

The conventional method for detecting objects in the 3D mammogram is to process the 2D slice image of the 3D mammogram. For example, the pixel features of the 2D slice image, such as the texture and the brightness, are taken as the parameters to analyze, and further, the selected pixels of the 2D slice image are used to detect the object of the 3D mammogram. However, the conventional method analyzes the 2D slice images. When the ranges of the 2D slice image, which are determined to contain the object, are spliced to recover the 3D mammogram, however, the border of the object range in the 3D mammogram is not continuous. The method reduces the precision for detecting the object range of the 3D mammogram.

The conventional method for detecting objects in the 3D mammogram includes the deep learning algorithm, the machine learning algorithm, and so on. The algorithm requires a large amount of feature data to train the model. If the amount of data is not enough, the problem that the model is over-fitting or under-fitting will occur.

On the other hand, the conventional method for detecting objects in the 3D mammogram uses the deep learning algorithm, the machine learning algorithm, and so on. The algorithm applies a single decision, such that the efficiency to detect the objects in the 3D mammogram is affected by the model efficiency of the algorithm's feature.

The problem that the area of the object in the 3D mammogram is recovered from the area of the object which is detected in the 2D slice image such that the range of the object in the 3D mammogram is not continuous to cause that the detecting result is not precise, the problem that the amount of feature data is not enough such that the model is over-fitting or under-fitting, and the problem that the single decision reduces the efficiency for detecting the object. Accordingly, how to find the solutions is an ordeal faced by people skilled in the art.

SUMMARY

The disclosure can be more fully understood by reading the following detailed description of the embodiments, with reference made to the accompanying drawings as described below. It should be noted that the features in the drawings are not necessarily to scale. The dimensions of the features may be arbitrarily increased or decreased for clarity of discussion.

The present disclosure of an embodiment provides an object detection method suitable for a 3D mammogram. The 3D mammogram includes a plurality of voxels. The object detection method includes steps of: controlling N filers to execute a filtering computation in the 3D mammogram respectively to generate N 3D filtering images, where N is an integer larger than 1; computing a difference value between Mth and (M−1)th 3D filtering images to generate a plurality of 3D differential images, where M is an integer between 1 and N; executing a filtering computation in the plurality of 3D differential images to generate a plurality of 3D smooth differential images; computing a difference variation among the plurality of voxels of the plurality of 3D smooth differential images to obtain a blurriness value of the plurality of voxels; using the blurriness value of the plurality of voxels in a decision module to execute a plurality of first decision operators to generate a plurality of first decision results, and using one or the plurality of first decision results to execute the plurality of second decision operators to generate a plurality of second decision results; and executing a final decision operator by using the plurality of first decision results and the plurality of second decision results to generate a detection object of the 3D mammogram.

One aspect of the present disclosure is to provide an object detection system. The object detection system includes a storage device and a processor. The storage device is configured to store a 3D mammogram. The 3D mammogram includes a plurality of voxels. The processor is connected with the storage device, and the processor includes N filters, a plurality of differential image operators, a blurriness value computation operator, and a decision module. The N filters are configured to execute a filtering computation in the 3D mammogram respectively to generate N 3D filtering images, where N is an integer larger than 1. The plurality of differential image operators is connected with the N filters, and the plurality of differential image operators is configured to compute a difference value between Mth and (M−1)th 3D filtering images to obtain a plurality of 3D differential images, where M is an integer between 1 and N. The blurriness value computation operator is connected with the plurality of differential image operators, and the blurriness value computation operator is configured to use the plurality of 3D differential images to execute a filter to generate a plurality of 3D smooth differential images. The blurriness value computation operator is further configured to compute a difference variation among the plurality of 3D smooth differential images to obtain a blurriness value of the plurality of voxels. The decision module is connected with the blurriness value computation operator, and the decision module is configured to use the blurriness value of the plurality of voxels to execute a plurality of first decision operators to generate a plurality of first decision results and use one or the plurality of first decision results to execute a plurality of second decision operators to generate a plurality of second decision results and to execute a final decision operator by using the plurality of first decision results and the plurality of second decision results to generate a detection object of the 3D mammogram.

One aspect of the present disclosure is to provide a non-transitory computer-readable storage medium storing computer-executable code including instructions for causing a processor to: acquiring a 3D mammogram comprising a plurality of voxels; controlling N filers to execute a filtering computation in the 3D mammogram respectively to generate N 3D filtering images, where N is an integer larger than 1; computing a difference value between Mth and (M-1)th 3D filtering images to generate a plurality of 3D differential images, where M is an integer between 1 and N; executing a filtering computation in the plurality of 3D differential images to generate a plurality of 3D smooth differential images; computing a difference variation among the plurality of 3D smooth differential images to obtain a blurriness value of the plurality of voxels; using the blurriness value of the plurality of voxels in a decision module to execute a plurality of first decision operators to generate a plurality of first decision results, and using one or the plurality of first decision results to execute the plurality of second decision operators to generate a plurality of second decision results; and executing a final decision operator by using the plurality of first decision results and the plurality of second decision results to generate a detection object of the 3D mammogram.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiments, with reference made to the accompanying drawings as described below. It should be noted that the features in the drawings are not necessarily to scale. The dimensions of the features may be arbitrarily increased or decreased for clarity of discussion.

DETAILED DESCRIPTION

The technical terms "first", "second" and the similar terms are used to describe elements for distinguishing the same or similar elements or operations and are not intended to limit the technical elements and the order of the operations in the present disclosure. Furthermore, the element symbols/alphabets can be used repeatedly in each embodiment of the present disclosure. The same and similar technical terms can be represented by the same or similar symbols/alphabets in each embodiment. The repeated symbols/alphabets are provided for simplicity and clarity and they should not be interpreted to limit the relation of the technical terms among the embodiments.

Figure 1:
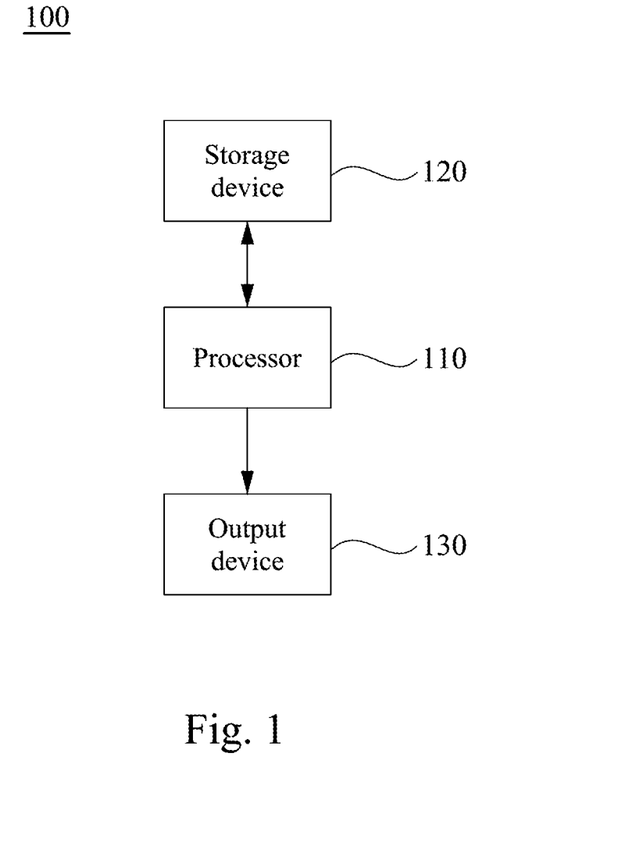
FIG. 1 is a block diagram illustrating an object detection system according to some embodiments of the disclosure.

Reference is made to FIG. 1. FIG. 1 is a block diagram illustrating an object detection system 100 according to some embodiments of the disclosure. As shown in FIG. 1, the object detection system 100 includes a processor 110, a storage device 120, and an output device 130. The processor 110 is electrically connected with the storage device 120 and the output device 130. The storage device 120 stores a 3D mammogram. For example, the 3D mammogram is a digital breast tomosynthesis (DBT). In some embodiments, the 3D mammogram includes a plurality of voxels (or called volume elements). The voxel in the disclosure is a basic element of the 3D mammogram which is data of 3D image coordinate (x,y,z).

In some embodiments, the object detection system 100 is configured to detect an object in the 3D mammogram. The object of the disclosure means the breast lesion, for example, the mass, the calcification, and so on. It should be noted that the object of the disclosure is not limited herein. The object detection system 100 computes a blurriness value of the 3D mammogram and trains a decision operator of a decision module by using the blurriness value and/or a combination of feature values. Therefore, the image analysis method can be applied for an indicated object, such as the mass, to detect the mass in the 3D mammogram. In some embodiments, the output device 130 is the display device. If the processor 110 detects the mass or the calcification in the 3D mammogram, the processor 110 tags a range of the mass or the calcification, and the output device 130 displays the coordinates of the range which covers the breast lesion in the 3D mammogram. For the sake of simplicity, the term "object" in the disclosure represents the image feature of the breast lesion.

Figure 2:
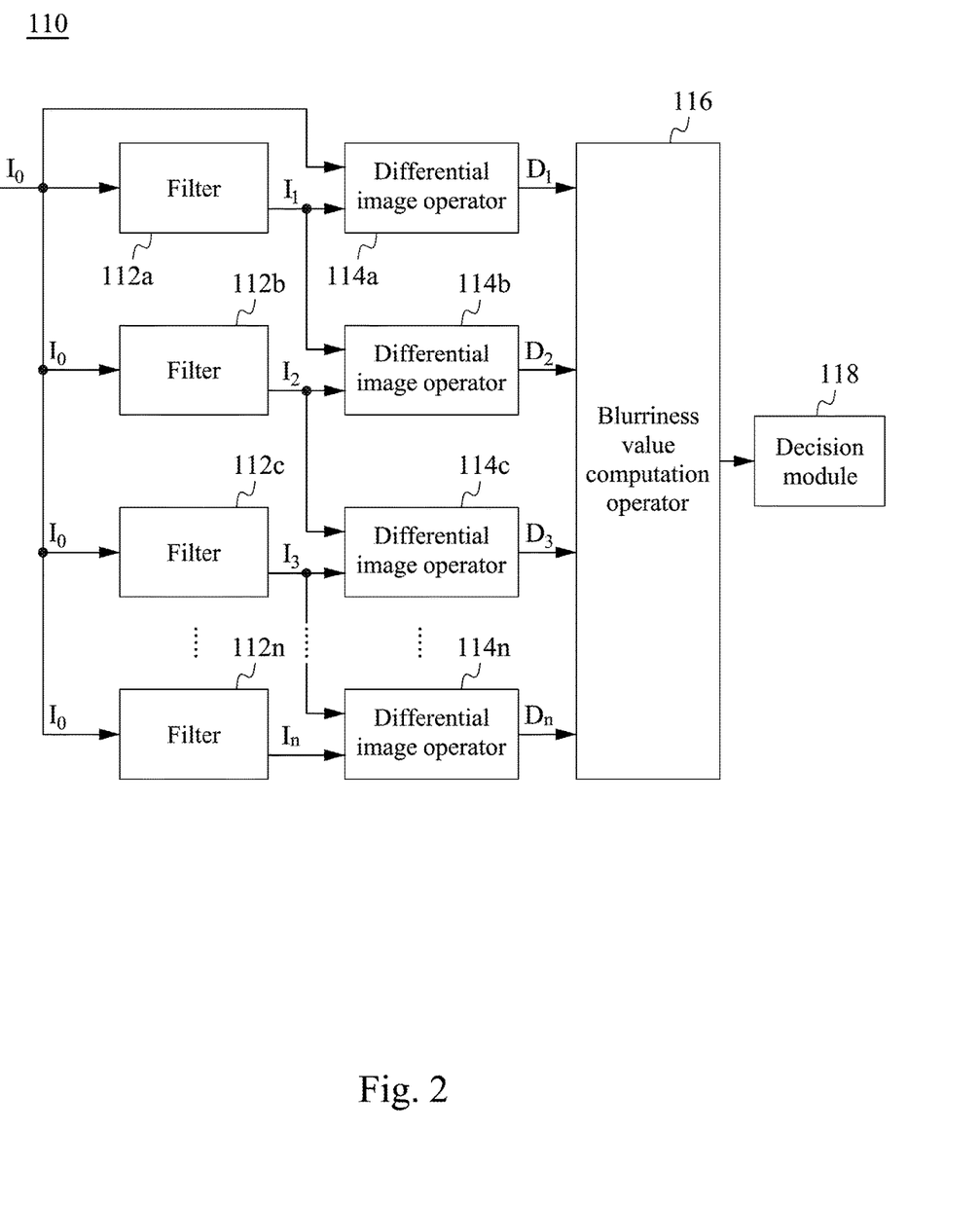
FIG. 2 is a block diagram illustrating a processor according to some embodiments of the disclosure.

Reference is made to FIG. 2. FIG. 2 is a block diagram illustrating the processor 110 according to some embodiments of the disclosure. As shown in FIG. 2, the processor 110 includes N filters 112a-112n, N differential image operators 114a-114n, a blurriness value computation operator 116, and a decision module 118. The filters 112a-112n are connected with the differential image operators 114a-114n respectively. The differential image operators 114a-114n are connected with the blurriness value computation operator 116. The blurriness value computation operator 116 is connected with the decision module 118. In some embodiments, the filters 112a-112n are averaging filters, Gaussian low-pass filters, band-stop filters, and so on. The type of filters 112a-112n is not limited herein.

In some embodiments, the N filters 112a-112n apply different parameters such that the N filters 112a-112n generate different filtering results.

Figure 3:
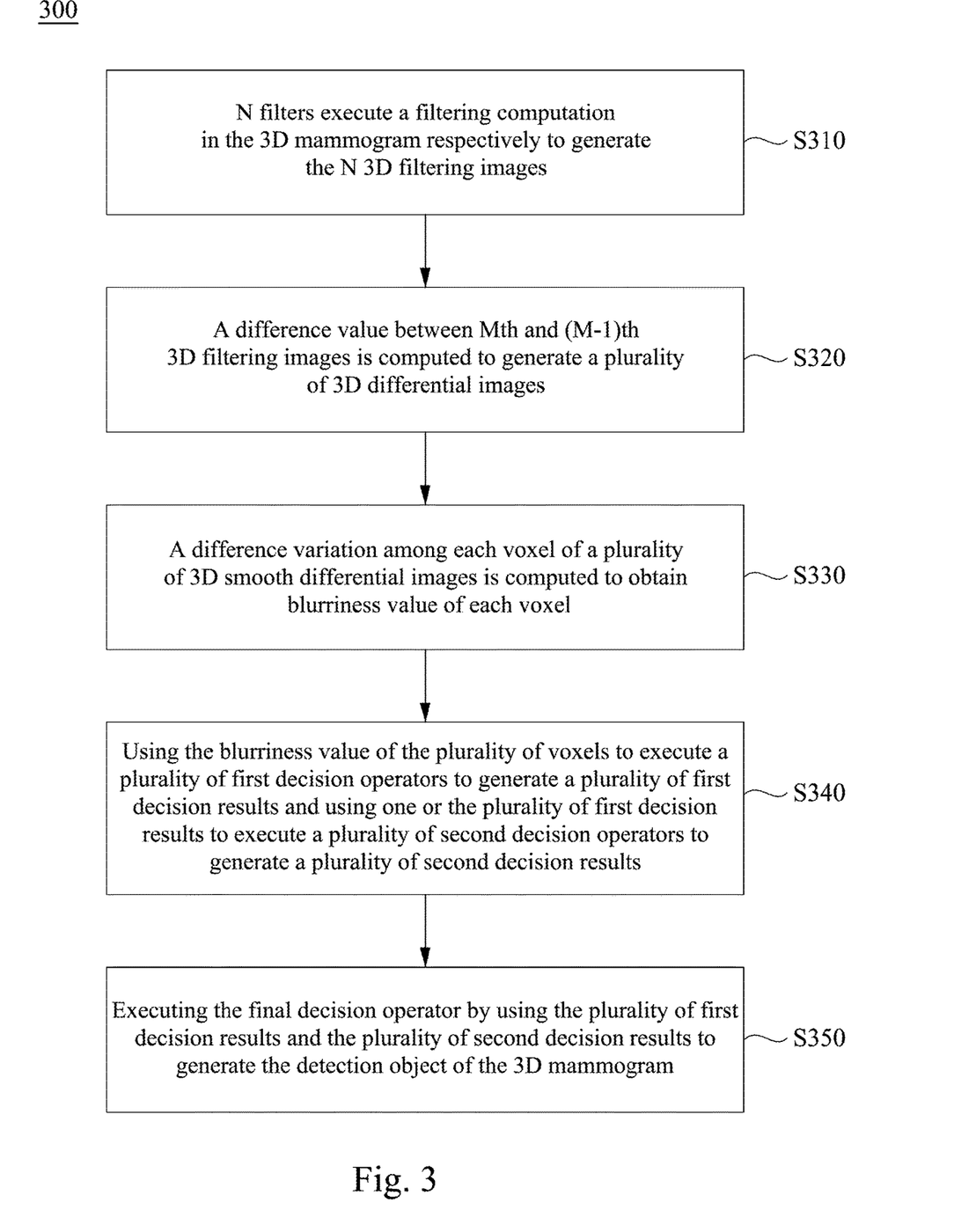
FIG. 3 is a flow chart illustrating an object detection method according to some embodiments of the disclosure.

Reference is made incorporating with FIG. 2 and FIG. 3. FIG. 3 is a flow chart illustrating an object detection method 300 according to some embodiments of the disclosure. The object detection method 300 is suitable for detecting the 3D mammogram. In some embodiments, the object detection system 100 is configured to execute each step of the object detection method 300.

In step S310, the N filters 112a-112n execute a filtering computation in the 3D mammogram respectively to generate the N 3D filtering images, where N is an integer larger than 1.

Reference is made to FIG. 2 again, after the N filters 112a-112n receive the 3D mammogram, the filters 112a-112n apply function 1 to generate the filtering images:

$$I_k = I_0 \otimes G_k \qquad \text{(function 1)}$$

, where $1 \leq k \leq N$. In function 1, $I_k$ is the kth filtering image, $G_k$ is the 3D Gaussian low-pass filters, and the operator $\otimes$ is the convolution operator. The parameter $G_k$ of function 1 is computed by function 2:

$$G_k = g^x \otimes g^y \otimes g^z \qquad \text{(function 2)}$$

In function 2, $g^x$, $g^y$, and $g^z$ are 1-dimension Gaussian low-pass filters, where $g^x$ is applied for the filter of x-direction of the 3D mammogram, $g^y$ is applied for the filter of y-direction filter of the 3D mammogram, and $g^z$ is applied for the filter of z-direction of the 3D mammogram. The parameter $g^x$ of function 2 is computed by function 3:

$$g^x(i) = \frac{1}{\alpha_x} e^{\frac{-\left(i - \frac{L_x}{2} + 0.5\right)^2}{2\sigma_x^2}} \quad \text{(function 3)}$$

In function 3, $\sigma_x$ is the standard deviation of $g^x$, and $L_x$ is the length of $g^x$. $\alpha_x$ is a weighting factor of $g^x$, and $\alpha_x$ is computed by function 4:

$$\alpha_x = \Sigma_{i=0}^{L_x-1} g^x(i) \quad \text{(function 4)}$$

Similarly, $g^y$ and $g^z$ are also computed by both function 3 and function 4.

Based on the said function 1 to function 4, after the filtering computation of the N filters is executed in the 3D mammogram respectively, N 3D filtering images $I_1, \ldots, I_n$ are generated.

In step S320, a difference value between Mth and (M−1)th 3D filtering images is computed to generate a plurality of 3D differential images.

Reference is made to FIG. 2 again. The differential image operators 114a-114n compute the difference value between two adjacent 3D filtering images. For example, the differential image operator 114m receives the Mth and the (M−1)th 3D filtering images to compute the difference value between the Mth and the (M−1)th 3D filtering images to generate the Mth 3D differential image, where M is an integer between 1 and N. As shown in FIG. 2, the differential image operator 114b generates the 3D differential image $D_2$, and the differential image operator 114c generates the 3D differential image $D_3$. Similarly, the differential image operator 114n generates the 3D differential image $D_n$. The differential image operator 114a computes the difference value between the 3D mammogram $I_0$ and the 3D filtering image $I_1$ to generate the 3D differential image $D_1$. In some embodiments, the N 3D differential images $D_1, \ldots, D_n$ are computed by function 5:

$$D_k = |I_{k-1} - I_k| \quad \text{(function 5)}$$

, where $1 \leq k \leq N$ and the operator "||" is the absolute value operator.

In step S330, based on each voxel of the 3D mammogram, a difference variation among each voxel of a plurality of 3D smooth differential images is computed to obtain a blurriness value of each voxel.

Reference is made to FIG. 2 again. The blurriness value computation operator 116 receives the N 3D differential images and executes the filter computation of the filters in the N 3D differential images to generate the N 3D smooth differential images. The filter can be, but not limited to, the averaging filter, the Gaussian low-pass filter, and so on. In some embodiments, the N 3D smooth differential images $H_1, \ldots H_n$ are computed by function 6:

$$H_k = D_k \otimes \Omega, \quad \text{(function 6)}$$

In function 6, $\Omega$ is a 3D averaging filter. The difference variation among each of the voxels of the plurality of 3D smooth differential images to obtain the blurriness value of the voxels. The blurriness value of the voxel is computed by function 7:

$$B = \Sigma_{i=1}^{N} w_i H_i \quad \text{(function 7)}$$

In function 7, B is a blurriness value image, and $w_i$ is a weighting value corresponding to the ith 3D smooth differential image. In the disclosure, the difference variation between a center voxel and the voxels around the center voxel is calculated by a numerical estimation. The larger the blurriness value is, the difference variation between the center voxel and the voxels around the center voxel is smaller, such that the visual effect is soft. The smaller the blurriness value is, the difference variation between the center voxel and the voxels around the center voxel is larger, such that the visual effect is sharp.

When the type of the breast lesion is different, the image feature of the 3D mammogram is also different accordingly (such as the object size, the brightness distribution, the texture, the contour). For example, the size of the mass is larger than the size of the calcification, and the distribution of the mass is more collective than the distribution of the calcification. The quantity of the calcification is more than the quantity of the mass. Based on the type of breast lesion, the filter parameters of function 1 to function 7 have to be set for the computations according to the object type which is assigned to detect the 3D mammogram. In some embodiments, the filters 112a-112n apply the 3D Gaussian low-pass filter, where a is the standard deviation, i.e., $\sigma_x = \sigma_y = \sigma_z = \sigma$. The 3D Gaussian low-pass filter uses the correct standard deviation, and the 3D mammogram is processed by the correct filter to generate the correct 3D filtering image, the correct 3D differential image, the correct 3D smooth differential image, and the correct blurriness value image. Accordingly, the object is detected correctively.

In some embodiments, the object detection method for detecting the mass applies four 3D Gaussian low-pass filters, and the four 3D Gaussian low-pass filters apply the standard deviations which are $\sigma_1 = 3$, $\sigma_2 = 7$, $\sigma_3 = 11$, $\sigma_4 = 15$. In some embodiments, the object detection method for detecting the calcification applies four 3D Gaussian low-pass filters, and the Gaussian low-pass filters apply the standard deviations which are $\sigma_1 = 3$, $\sigma_2 = 5$, $\sigma_3 = 7$, $\sigma_4 = 9$. That is, the plurality of 3D Gaussian low-pass filters apply different standard deviations based on the object type. In some embodiments, the N standard deviations a $\sigma_1, \sigma_2, \ldots, \sigma_n$ of the N 3D Gaussian low-pass filters satisfy the requirement: $\sigma_1 < \sigma_2 < \ldots < \sigma_n$.

In step S340, using the blurriness value of the plurality of voxels to execute a plurality of first decision operators to generate a plurality of first decision results and using one or the plurality of first decision results to execute a plurality of second decision operators to generate a plurality of second decision results is performed.

Figure 4:
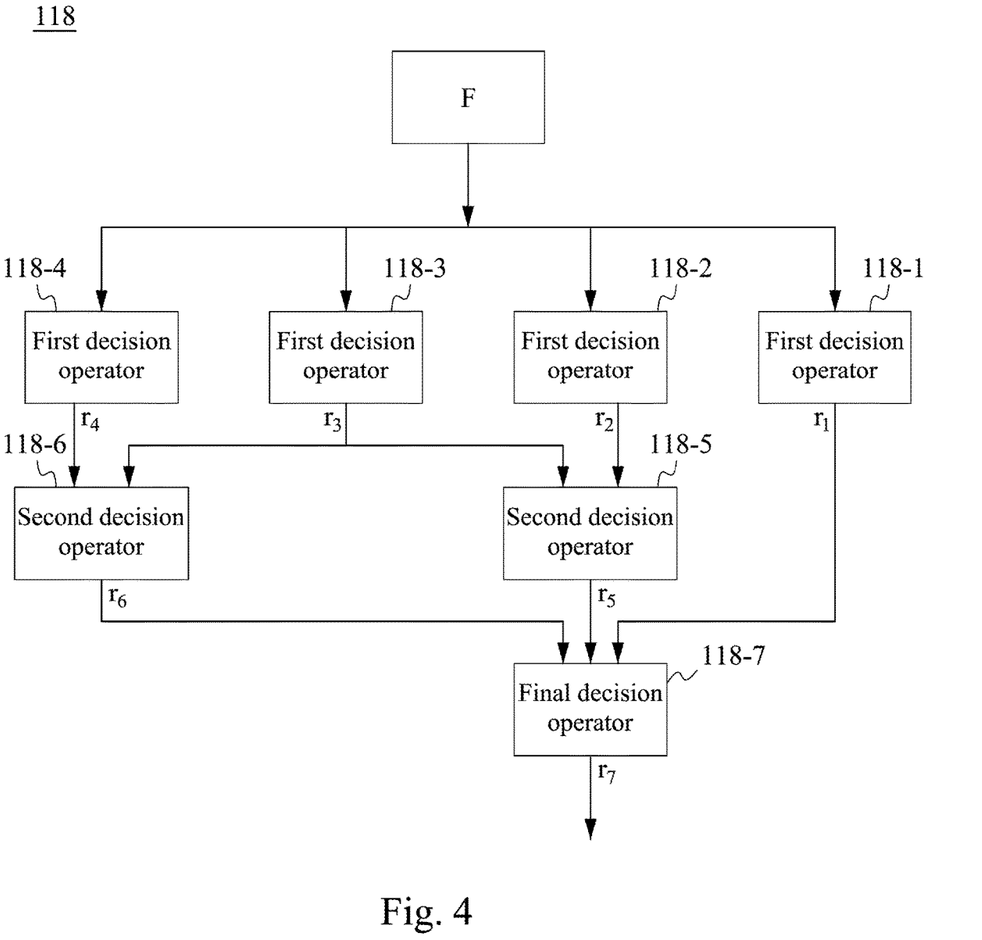
FIG. 4 is a block diagram illustrating a decision module according to some embodiments of the disclosure.

Reference is made incorporating with FIG. 2 to FIG. 4. FIG. 4 is a block diagram illustrating the decision module 118 according to some embodiments of the disclosure. It should be noted that the decision module 118 is shown as an example and its circuit or structure is not limited herein, a person of ordinary skill in the art can change the number of the elements in each layer of the decision module 118 and increase/decrease the number of the layers of the decision module 118 by practical demands. As shown in FIG. 4, the decision module 118 includes a plurality of first decision operators 118-1, 118-2, 118-3, 118-4, a plurality of second decision operators 118-5, 118-6, and a final decision operator 118-7. Each decision operator includes a different rule. In the training stage for the decision operator, each decision operator trains the training feature data and a tag of the object type corresponding to the training feature data based on the rule of each decision operator. In some embodiments, the first decision operators 118-1 to 118-4, the second decision operators 118-5 to 118-6, and the final decision operator 118-7 execute the regression, the classification, the voting process, and so on. For example, the first decision operators 118-1 and 118-4 are configured to execute the classification, and the first decision operators 118-2 and 118-3 are configured to execute the regression. The second decision operator 118-5 is configured to execute the binary classification, and the second decision operator 118-6 is configured to execute the regression. The final decision operator 118-7 is configured to execute the voting process.

The decision module 118 receives the feature data F. In some embodiments, the feature data F makes use of the blurriness value which is outputted by the blurriness value computation operator 116. In some other embodiments, the feature data F makes use of a combination of the blurriness value and other features.

As shown in FIG. 4, in some embodiments, the decision module 118 inputs the blurriness value of the voxel to the first decision operators 118-1 to 118-4 to generate the first decision results $r_1, \ldots, r_4$ respectively. And then the second decision operator 118-5 receives the first decision results $r_2$ and $r_3$ and executes the decision operation to generate the second decision result $r_5$. The second decision operator 118-6 receives the first decision results $r_3$ and $r_4$ and executes the decision operation to generate the second decision result $r_6$. Each decision operator can connect the relationship between features of the 3D mammogram and the object type. In some other embodiments, each decision operator can make use of the combination of the blurriness value and other features of the 3D mammogram to execute the decision operation.

Reference is made incorporating with FIG. 3 and FIG. 4. In step S350, executing the final decision operator by using the plurality of first decision results and the plurality of second decision results to generate the detection object of the 3D mammogram is performed. In some embodiments, the final decision operator 118-7 receives the first decision result $r_1$ and the second decision results $r_5$ and $r_6$, and executes the decision operation to generate the final decision result $r_7$.

The decision module in the disclosure, which is different from the conventional method that uses a single decision strategy, applies the plurality of decision operators, such as the regression, the classification, the voting process. The plurality of first decision results generated by the plurality of decision operators can be the regression values, the classification results, the voting results, and so on. And then the decision results are processed by one or more decision operators, and one or more second decision results are generated. That is, the decision operation is performed based on the previous decision results. The final decision operator generates the detection result of the object. Therefore, in the object detection procedure, the processor 110 detects the object in a detecting 3D mammogram, and the object can be the mass and the calcification. The term "a detecting 3D mammogram" is an image that is going to be detected whether the object exists thereon.

In some embodiments, when the processor 110 detects the object of the detecting 3D mammogram, the range of the object will be generated. Reference is made to FIG. 1 again, the output device 130 displays the range of the object in the detecting 3D mammogram for people to refer. The range is a 3D image range, and the user can get the information on the size and the location of the lesion through the output device 130.

Figure 5:
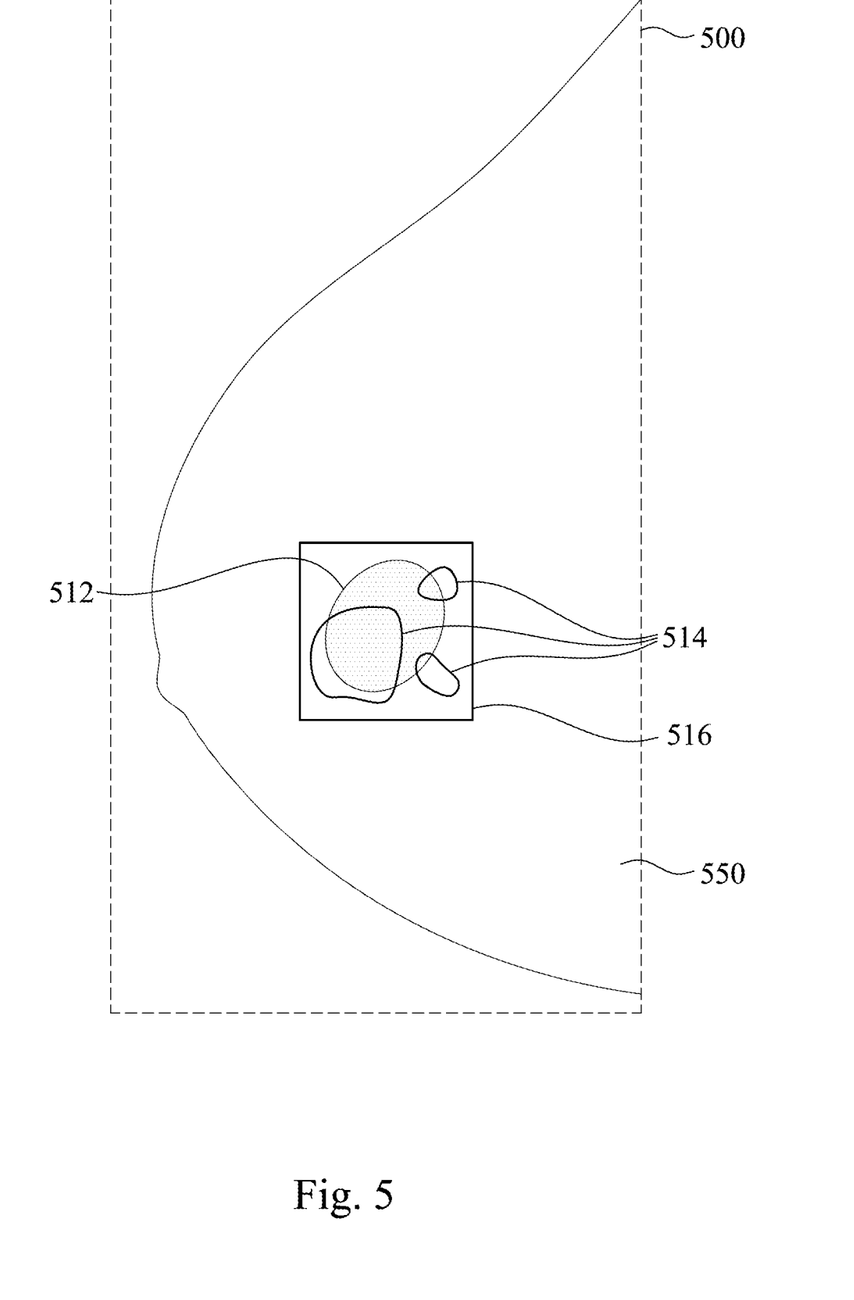
FIG. 5 is a diagram illustrating a detection result of the mass in a 2D slice image which is part of a 3D mammogram according to some embodiments of the disclosure.

Reference is made to FIG. 5. FIG. 5 is a diagram illustrating the detection result of the mass in a 2D slice image 500 which is a part of a 3D mammogram according to some embodiments of the disclosure. As shown in FIG. 5, the numeral 550 of the 2D slice image 500 is the side view of the breast. In the embodiment, the mass is detected in the detecting 3D mammogram. The physiological range of the mass is shown as the numeral 512, the detected range of the mass is shown as the numeral 514, and the range marked by professional doctors is shown as the numeral 516.

Figure 6:
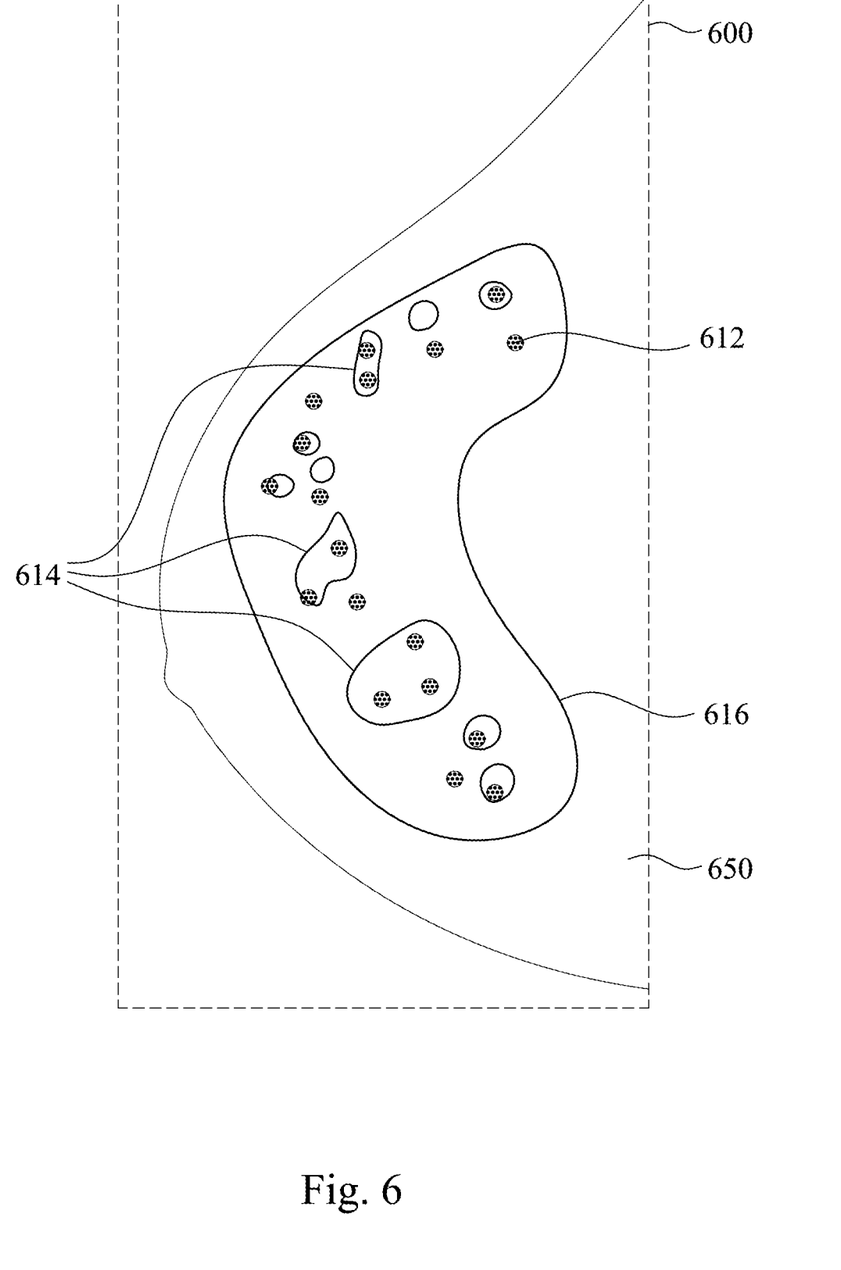
FIG. 6 is a diagram illustrating a detection result of the calcification in a 2D slice image which is part of a 3D mammogram according to some embodiments of the disclosure.

FIG. 6 is a diagram illustrating a detection result of the calcification in a 2D slice image 600 which is a part of a 3D mammogram according to some embodiments of the disclosure. As shown in FIG. 6, the numeral 650 of the 2D slice image 600 is the side view of the breast. In the embodiment, the calcification is detected in the detecting 3D mammogram. The physiological range of the calcification is shown as the numeral 612, the detected range of the calcification, which is shown as the numeral 614, has small volume and spreads loosely. The range of the calcification in FIG. 6 is shown by the 3 numerals 614 as the representation a part of the affections, and other calcification parts are not numbered for the sake of concise. In FIG. 6, the range marked by professional doctors is shown as the numeral 616.

The range 514 denoted as the detection object of FIG. 5 and the range 614 denoted as the detection object of FIG. 6 is the 3D image range. In the figures, the 2D slice image is taken as an example for illustrating the 3D image range. Because the object detection method provides how to retrieve the range of the lesion of the 3D mammogram, the disclosure is not limited to the 2D slice image drawn in the figures.

In some embodiments, a non-transitory computer-readable storage medium that stores multiple executable codes including instructions is provided. The executable code is loaded into the processor 110 of FIG. 1 and the processor 110 executes the instructions to execute steps in FIG. 3. For example, the processor 110 acquires the 3D mammogram including the plurality of voxels, controls the N filers to execute the filtering computation respectively to generate N 3D filtering images, computes the difference value between Mth and (M−1)th 3D filtering images to generate the plurality of 3D differential images, executes the filtering computation in the plurality of 3D differential images to generate a plurality of 3D smooth differential images, computes the difference variation among the plurality of 3D smooth differential images to obtain the blurriness value of the plurality of voxels, and uses the decision module to detect the object in the 3D mammogram.

Accordingly, the object detection method, the object detection system suitable for the 3D mammogram, and the non-transitory computer-readable storage medium compute the blurriness value of the voxels of the 3D mammogram to determine whether the voxel is a part of the object and then to detect the object of the 3D mammogram. Because of the imaging features of the 3D mammogram, the computed blurriness value can be represented as the feature of the imaging focus of the object, and the feature is equivalent to the depth information of the 3D image. Therefore, the blurriness value of the voxel can be used to detect the object in the 3D mammogram. For example, the imaging of the mass is blurry, and the range of the mass in the 3D mammogram includes the voxels which have large blurriness value. The imaging of the calcification is definite, and the range of the calcification in the 3D mammogram includes the voxels which have small blurriness value. Furthermore, because the decision module in the disclosure combines the plurality of decision operators, the problem of the over-fitting model or the under-fitting model for determining the voxels of the 3D mammogram can be resolved.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An object detection method for a 3D mammogram, the 3D mammogram comprising a plurality of voxels, wherein the object detection method comprises:
controlling N filters to execute a filtering computation in the 3D mammogram respectively to generate N 3D filtering images, wherein N is an integer larger than 1;
computing a difference value between Mth and (M−1)th 3D filtering images to generate a plurality of 3D differential images, wherein M is an integer between 1 and N;
executing a filtering computation in the plurality of 3D differential images to generate a plurality of 3D smooth differential images;
computing a difference variation among the plurality of 3D smooth differential images to obtain a blurriness value of the plurality of voxels;
using the blurriness value of the plurality of voxels in a decision module to execute a plurality of first decision operators to generate a plurality of first decision results, and using one or the plurality of first decision results to execute the plurality of second decision operators to generate a plurality of second decision results; and
executing a final decision operator by using the plurality of first decision results and the plurality of second decision results to generate a detection object of the 3D mammogram.

2. The object detection method of claim 1, further comprising:
setting an object type corresponding to the plurality of voxels, wherein the object type comprises a mass and a calcification.

3. The object detection method of claim 1, wherein step of generating the N 3D filtering images comprises:
executing a filtering computation of N 3D Gaussian low-pass filters in the 3D mammogram to generate the N 3D filtering images.

4. The object detection method of claim 3, wherein N standard deviations of the N 3D Gaussian low-pass filters are $\sigma_1, \sigma_2, \ldots, \sigma_n$.

5. The object detection method of claim 3, wherein N standard deviations of the N 3D Gaussian low-pass filters satisfy $\sigma_1 < \sigma_2 < \ldots < \sigma_n$.

6. The object detection method of claim 1, wherein step of obtaining the plurality of 3D differential images comprises:
computing a difference value between two adjacent 3D filtering images to obtain the plurality of 3D differential images.

7. The object detection method of claim 6, further comprising:
computing the difference value between Mth and (M−1)th 3D filtering images to generate an Mth 3D differential image.

8. The object detection method of claim 1, wherein step of obtaining the blurriness value of the plurality of voxels comprises:
computing the difference variation among the plurality of 3D smooth differential images to obtain the blurriness value of the plurality of voxels.

9. The object detection method of claim 8, further comprising:
executing a filtering computation of a 3D low-pass filter in the plurality of 3D differential images to generate the plurality of 3D smooth differential images.

10. The object detection method of claim 9, wherein the 3D low-pass filter comprises an averaging filter.

11. The object detection method of claim 8, further comprising:
obtaining a weighting value corresponding to each of the plurality of 3D smooth differential images; and
setting a summation of the each of the plurality of 3D smooth differential images and the weighting value as the blurriness value.

12. The object detection method of claim 1, wherein when a determination is made that a detected 3D mammogram comprises the detection object, a range which comprises the detection object is denoted in the detected 3D mammogram.

13. An object detection system, comprising:
a storage device configured to store a 3D mammogram, wherein the 3D mammogram comprises a plurality of voxels; and
a processor connected with the storage device, wherein the processor comprises:
N filters configured to execute a filtering computation in the 3D mammogram respectively to generate N 3D filtering images, wherein N is an integer larger than 1;
a plurality of differential image operators connected with the N filters, wherein the plurality of differential image operators is configured to compute a difference value between Mth and (M−1)th 3D filtering images to obtain a plurality of 3D differential images, wherein M is an integer between 1 and N;
a blurriness value computation operator connected with the plurality of differential image operators, wherein the blurriness value computation operator is configured to use the plurality of 3D differential images to execute a filter to generate a plurality of 3D smooth differential images, wherein the blurriness value computation operator is further configured to compute a difference variation among the plurality of voxels of the plurality of 3D smooth differential images to obtain a blurriness value of the plurality of voxels; and
a decision module connected with the blurriness value computation operator, wherein the decision module is configured to use the blurriness value of the plurality of voxels to execute a plurality of first decision operators to generate a plurality of first decision results, use one or the plurality of first decision results to execute a plurality of second decision operators to generate a plurality of second decision results, and execute a final decision operator by using the plurality of first decision results and the plurality of second decision results to generate a detection object of the 3D mammogram.

14. The object detection system of claim 13, wherein the decision module is further configured to:
set an object type corresponding to the plurality of voxels, wherein the object type comprises a mass and a calcification.

15. The object detection system of claim 13, wherein the N filters comprises N 3D Gaussian low-pass filters, wherein the N 3D Gaussian low-pass filters are configured to execute a filtering computation in the 3D mammogram to generate the N 3D filtering images.

16. The object detection system of claim 15, wherein N standard deviations of the N 3D Gaussian low-pass filters are $\sigma_1, \sigma_2, \ldots, \sigma_n$.

17. The object detection system of claim 15, wherein N standard deviations of the N 3D Gaussian low-pass filters satisfy $\sigma_1 < \sigma_2 < \ldots < \sigma_n$.

18. The object detection system of claim 13, wherein the blurriness value computation operator is further configured to:
   compute a difference value among the plurality of voxels of the plurality of 3D smooth differential images to obtain the blurriness value of the plurality of voxels.

19. The object detection system of claim 18, wherein a 3D low-pass filter comprises an averaging filter, and the averaging filter executes the filtering computation in the plurality of 3D differential images to generate the plurality of 3D smooth differential images.

20. The object detection system of claim 18, wherein the decision module is further configured to:
   obtain a weighting value corresponding to each of the plurality of 3D smooth differential images; and
   set a summation of the plurality of 3D smooth differential images and the weighting value as the blurriness value.

21. The object detection system of claim 13, wherein the processor is further configured to:
   when determining that a detected 3D mammogram comprises the detection object, tag a range which comprises the detected 3D mammogram.

22. A non-transitory computer-readable storage medium storing computer-executable code comprising instructions for causing a processor to:
   acquire a 3D mammogram comprising a plurality of voxels;
   control N filters to execute a filtering computation in the 3D mammogram respectively to generate N 3D filtering images, wherein N is an integer larger than 1;
   compute a difference value between Mth and (M−1)th 3D filtering images to generate a plurality of 3D differential images, wherein M is an integer between 1 and N;
   execute a filtering computation in the plurality of 3D differential images to generate a plurality of 3D smooth differential images;
   compute a difference variation among the plurality of 3D smooth differential images to obtain a blurriness value of the plurality of voxels;
   use the blurriness value of the plurality of voxels in a decision module to execute a plurality of first decision operators to generate a plurality of first decision results, and use one or the plurality of first decision results to execute the plurality of second decision operators to generate a plurality of second decision results; and
   execute a final decision operator by using the plurality of first decision results and the plurality of second decision results to generate a detection object of the 3D mammogram.

* * * * *